(12) United States Patent
Carnell

(10) Patent No.: US 7,435,338 B2
(45) Date of Patent: Oct. 14, 2008

(54) REMOVAL OF MERCURY COMPOUNDS FROM GLYCOL

(75) Inventor: Peter John Herbert Carnell, Cleveland (GB)

(73) Assignee: Johnson Matthey PLC, London (GB)

( * ) Notice: Subject to any disclaimer, the term of this patent is extended or adjusted under 35 U.S.C. 154(b) by 418 days.

(21) Appl. No.: 10/575,555

(22) PCT Filed: Oct. 29, 2004

(86) PCT No.: PCT/GB2004/004593

§ 371 (c)(1),
(2), (4) Date: Apr. 10, 2006

(87) PCT Pub. No.: WO2005/047438

PCT Pub. Date: May 26, 2005

(65) Prior Publication Data
US 2007/0134143 A1 Jun. 14, 2007

(30) Foreign Application Priority Data
Nov. 5, 2003 (GB) .................. 0325769.8
Jun. 24, 2004 (GB) .................. 0414160.2

(51) Int. Cl.
C10G 29/04 (2006.01)
(52) U.S. Cl. .................. 208/253; 208/251 R

(58) Field of Classification Search .......... 208/251 R, 208/253
See application file for complete search history.

(56) References Cited

U.S. PATENT DOCUMENTS

| | | | | |
|---|---|---|---|---|
| 4,986,898 A * | 1/1991 | Torihata et al. | .......... | 208/251 R |
| 5,062,948 A * | 11/1991 | Kawazoe et al. | ........ | 208/251 R |
| 5,080,799 A * | 1/1992 | Yan | ............................ | 210/661 |
| 6,475,451 B1 | 11/2002 | Leppin et al. | | |
| 2002/0198097 A1 | 12/2002 | El-Shoubary et al. | | |
| 2006/0205591 A1* | 9/2006 | Lee et al. | .................... | 502/400 |

FOREIGN PATENT DOCUMENTS

FR 2 529 802 A1 1/1984
WO WO-00/56844 A1 9/2000

* cited by examiner

*Primary Examiner*—Tam M Nguyen
(74) *Attorney, Agent, or Firm*—RatnerPrestia

(57) ABSTRACT

The invention is a process for removing mercury compounds from a glycol- or alcohol-containing liquid absorbent stream which contains mercury compounds, especially a glycol stream which has been used in a glycol drying plant for removing water from natural gas streams. The process comprises contacting the mercury-laden liquid absorbent stream with a bed of solid absorbent particles, comprising a sulphided metal, optionally supported on support material, or sulphur supported on carbon.

12 Claims, 1 Drawing Sheet

REMOVAL OF MERCURY COMPOUNDS FROM GLYCOL

This application is the U.S. National Phase application of PCT International Application No. PCT/GB2004/004593, filed Oct. 29, 2004, and claims priority of British Patent Application No. 0325769.8, filed Nov. 5, 2003, and British Patent Application No. 0414160.2, filed Jun. 24, 2004.

FIELD OF THE INVENTION

The present invention relates to the removal of mercury compounds from mixtures of mercury and glycol and/or other alcohol compounds, in particular such mixtures which are formed during a drying process.

BACKGROUND OF THE INVENTION

In natural gas processing plants, the gas is treated to remove acid gases, sulphur compounds and water in order to produce a gas which is suitable for distribution to the end-user. The removal of water vapour from natural gas is essential in order to avoid the formation of hydrocarbon hydrates in the gas stream and also to avoid the water condensing out of the gas in pipelines and process equipment which may then lead to corrosion problems. For this reason the maximum amount of water allowable in processed natural gas is regulated. Several methods of removing water to depress the dew point of natural gas are practised commercially in gas-processing plants. The methods employed include contacting the gas with a bed of a solid desiccant such as a silica gel or molecular sieve, and the use of liquid desiccant compounds. In the latter case, a typical process involves contacting the wet gas stream with a glycol solution in order to strip water from the gas stream into the glycol solution. This process is known as glycol dehydration and is very widely used in gas processing operations. The glycol solution is regenerated (i.e. dried) by removing the water in a boiler or in a flash-tank apparatus and the resulting dry glycol is recycled back to the drying process.

In some drying processes, methanol or another alcohol may be used as an alternative to glycol or as a mixture with a glycol. Methanol in particular, optionally admixed with a glycol, is often used to dehydrate gas flowing out of a sub-sea well, where the formation of methane or ethane hydrates is a problem due to the cooling of the gas as it exits the well. The methanol and/or glycol is introduced directly into the pipeline, usually by spraying, in order to absorb water in the gas stream. The wet methanol and/or glycol is then separated from the gas at a location downstream of the injection point, usually at the associated gas processing plant, and then regenerated by drying, e.g. by distillation before being returned to the injection point.

Mercury compounds are found in petroleum fluids such as natural gas. The concentration of mercury in natural gas is dependent on the source and may vary from very low, e.g. about 10 $ngm^{-3}$ to high e.g. 5,000 $ngm^{-3}$ or more. When natural gas containing mercury compounds is dried in a glycol dryer, we have found that the mercury compounds tend to partition into the glycol and thence into the water and dissolved gases separated from the glycol during glycol drying and regeneration, during which process desorbed gas, water and mercury may be evolved. The drying of the glycol for regeneration is usually done by heating to an elevated temperature which is above the boiling point of water. The temperature used is selected to be lower than the boiling point of the glycol in order to avoid decomposition of the glycol which may occur on prolonged heating. Therefore the temperature used for regeneration depends on the boiling point and thermal stability of the glycol used, e.g. triethylene glycol may be regenerated at about 200° C. On cooling, the water in vented gas is condensed and discharged. The waste-water and desorbed gases may contain significant amounts of mercury and thereby pose an environmental problem on discharge.

Alcohols, particularly methanol may be used in other purification processes, for example in the Rectisol™ wash process which is used to remove sulphur compounds and $CO_2$ from gas streams, including hydrogen, ammonia or methanol syngas streams amongst others. Where the gas stream contains mercury or compounds of mercury, then the regeneration of the methanol wash liquid may risk discharge of the mercury to the atmosphere. Methanol absorbents may be regenerated by fractional distillation techniques in a conventional manner.

SUMMARY OF THE INVENTION

We have developed a method of reducing the mercury discharged to the atmosphere from process apparatus used for regenerating alcohol or glycol streams which have been used for purifying gas streams which may contain mercury or its compounds.

According to the invention, we provide a process for removing mercury compounds from a glycol- and/or alcohol-containing stream which contains said mercury compounds comprising the step of contacting said glycol- and/or alcohol-containing stream with a bed of solid absorbent particles, said absorbent particles comprising a sulphided metal, optionally supported on support material or sulphur supported on a carbon support.

According to a further aspect of the invention, we provide a process for removing water, sulphur compounds and/or carbon dioxide from a hydrocarbon-containing stream which additionally contains at least one compound of mercury or elemental mercury comprising:

a) contacting the hydrocarbon stream with a liquid absorbent stream, comprising a glycol and/or an alcohol, thereby to absorb at least some of the water, sulphur compounds and/or carbon dioxide and mercury from the hydrocarbon stream into the liquid absorbent stream, to form a loaded liquid absorbent stream which contains mercury compounds;

b) contacting said loaded liquid absorbent stream with a bed of solid absorbent particles, said absorbent particles comprising a sulphided metal, optionally supported on support material, or sulphur supported on a carbon support to form a treated liquid absorbent stream containing a reduced concentration of mercury compared with the loaded liquid absorbent stream c) optionally, drying the treated liquid absorbent stream, to form a liquid absorbent stream which may be recirculated to step a), optionally after mixing with a fresh liquid absorbent stream.

DETAILED DESCRIPTION OF THE INVENTION

Figure 1:
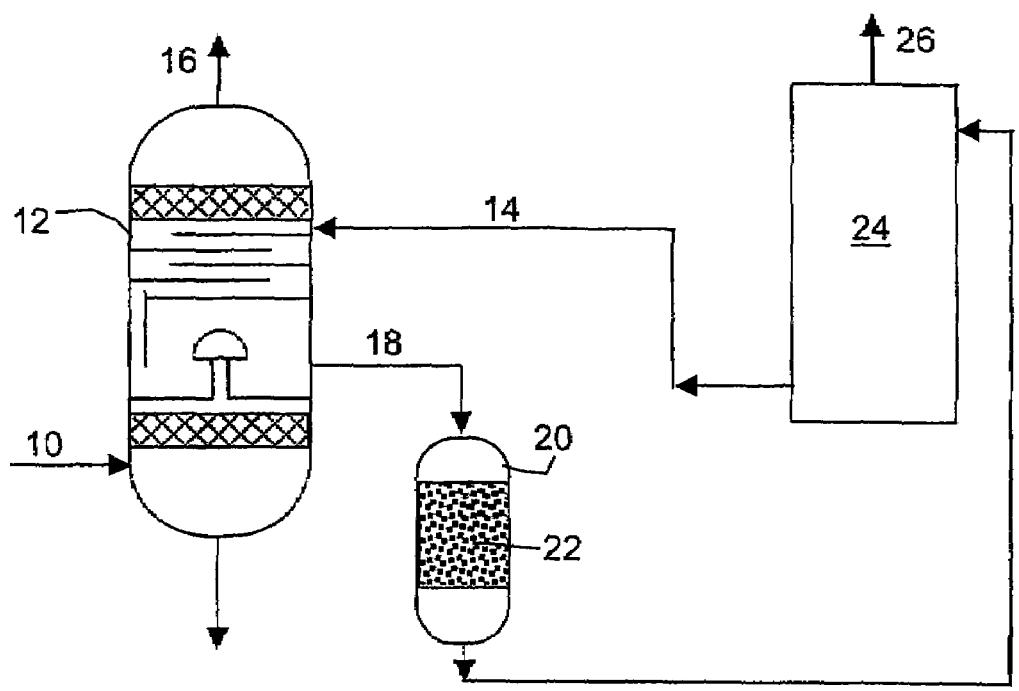
FIG. 1 is a schematic diagram of a glycol drying system incorporating an embodiment of the invention.

The sulphided metal may be any which provides a metal compound which shows a suitable capacity for being sulphided and for mercury absorption. Examples of suitable metals are iron, nickel and copper, and in particular copper and nickel. Optionally a mixture of metals is used. Certain other metals, however, are generally unable to provide either compounds which can be suitably sulphided, e.g. aluminium, or sulphided compounds which can adequately absorb mercury e.g. zinc. Nevertheless, a compound of such an other metal may be present as a binding or support agent which improves the structural integrity of the absorbent, and/or as a promoter which enhances the sulphiding of the precursor and/or the absorption of mercury by the absorbent. A particularly preferred other metal compound is a zinc oxide, carbonate or bicarbonate. Suitable binder materials include alumina and refractory cement compounds The absorbent comprising the sulphided metal compound may be in any suitable physical form, e.g. as a granule, extrudate, or tablet. Particularly effective absorbents are those which are prepared from unsulphided metal compounds having a capacity to be highly sulphided. Thus, it is preferred that the amount of sulphide-forming compound of the metal present in the precursor is such that the precursor may be sulphided to achieve a sulphur loading of at least 0.5% w/w, e.g. from 1-5% S, although higher loadings of sulphur may be provided, e.g. up to about 20% w/w or greater.

The absorbent particles may comprise a pre-sulphided absorbent comprising copper and/or nickel sulphide prepared by forming an absorbent precursor comprising a copper and/or nickel compound, e.g. an extrudate comprising basic copper carbonate and a binder which is e.g. a refractory cement, and then sulphiding the absorbent precursor. The sulphur compound used to sulphide the precursor may be one or more sulphur compounds such as hydrogen sulphide, carbonyl sulphide, mercaptans and polysulphides.

Alternatively an absorbent comprising a metal sulphide may be formed by concomitantly forming the metal sulphide during the absorption, of the mercury. Where the absorbent material comprising sulphided metal compounds is more difficult to handle than unsulphided absorbent, e.g. due to a weakening of the absorbent particles upon absorption of sulphur, it is preferred to use an unsulphided absorbent, i.e. an "absorbent precursor", and form the copper and/or nickel sulphides for the removal of mercury in situ. Since the glycol and/or alcohol may absorb sulphur compounds such as $H_2S$ or COS during the drying or purification of the hydrocarbon-containing gas stream to be treated, it is convenient to remove the sulphur compound(s) using a bed of a copper and/or nickel containing absorbent, thereby forming the metal sulphide in situ for removing the mercury compounds from the glycol. A metal compound suitable for use in an absorbent precursor is one which may be readily sulphided and may include the oxide, carbonate, and/or basic carbonate. A particularly suitable metal compound is basic copper carbonate. By absorbent precursor, we mean a compound which, following treatment with a sulphur-containing compound, forms the absorbent for absorbing the mercury and/or mercury compounds.

Where concomitant sulphiding and mercury absorption occurs, the amount of sulphur compound that is present depends on the type of sulphur compound and metal compound used. Usually, a concentration ratio, as defined by the ratio of sulphur compound (expressed as hydrogen sulphide) concentration (v/v) to mercury concentration (v/v), of at least one, and preferably of at least 10 is used so that the precursor is sufficiently sulphided. Should the initial concentration of the sulphur compound in the feed stream be below the level necessary to establish the desired ratio of sulphur compound to mercury compound concentration then it is preferred that the concentration of the sulphur compound is increased by any suitable method, e.g. by the addition of further quantities of the sulphur compound, or by the use of a molecular sieve or semi-permeable membrane to selectively increase the concentration of the sulphur compound.

Alternatively, or additionally, the absorbent material may comprise sulphur supported on a carbon support.

The process of the present invention may also be used to remove mercury from glycol which has been used to flush a contaminated pipeline in order to remove contaminants, including mercury and mercury compounds, from the pipeline itself. Such use may be required when it is desired to remove mercury from a pipeline e.g. prior to decommissioning.

The removal of mercury from the glycol/alcohol is effected by contacting the mercury-laden liquid absorbent with a bed of solid absorbent particles at sufficient pressure to induce flow through the bed. The contact of the liquid absorbent with solid absorbent particles may be effected at elevated pressure or at a pressure close to ambient. If the liquid absorbent stream is at a high pressure and is to be regenerated by drying at a lower pressure then the step of reducing the pressure may release gases which contain some dissolved mercury compounds. For this reason it may be preferable to contact the liquid absorbent stream with the solid absorbent particles at or near the pressure used for the dehydration, i.e. before the pressure is let-down for drying of the glycol or alcohol stream. Typically these pressures may be in the region of 300 bar or higher, e.g. up to 350 bar. Where the dispersal of mercury compounds on pressure reduction is not likely to occur or where the liquid glycol or alcohol stream is at a relatively low pressure, then the contact with the solid absorbent particles may take place at a lower pressure, e.g. in the range 1-50 bar. The contact temperature is normally less than about 50° C., usually at ambient temperature.

The glycols typically used in glycol drying plant include monoethylene glycol (MEG), diethylene glycol (DEG), triethylene glycol (TEG) and tetraethylene glycol (TREG). Triethylene glycol appears to be the most commonly used in the dehydration of natural gas. Methanol is commonly used in Rectisol wash processes and for removal of water from gas flows within the gas pipeline. Other alcohols, mixtures of alcohols and ethers may also be used and the process of the invention may be used to remove mercury from absorbent streams comprising these alcohols, glycols, ethers and mixtures provided they are compatible with the solid particulate mercury absorbent. By compatible, we mean that the liquid absorbent used must not cause rapid deterioration of the absorbent bed by dissolving or otherwise weakening the particles to any significant degree.

FIG. 1 shows a typical flow diagram for a glycol drying system incorporating the process of the invention. For simplicity, heat exchangers and circulation pumps have not been shown. In the drawing, a wet gas stream 10 enters a glycol drying tower 12 to contact a relatively dry glycol stream 14 as the gas flows upwardly through the column. The dried gas stream leaves the column via line 16. The wet glycol stream 18 leaves the tower and passes though a mercury absorber 20 containing a bed 22 of sulphided absorbent. The glycol then passes to a glycol regeneration unit 24 and the water is removed from the glycol by heating and the water and other contaminants are removed via line 26. In the process flowsheet, the bed of absorbent is advantageously located after the glycol contactor or after a flash tank (if present), the flash tank being used to remove absorbed gas from the glycol. The absorbent bed must be located so that the wet glycol contacts the absorbent before it is heated to regenerate the dry glycol.

The experiment will be further described with reference to the following examples.

EXAMPLE 1

A 3 g bead of elemental mercury was contacted with 15 ml of triethyleneglycol (TEG) in a 30 ml glass vial. The vial and contents were mixed for 2.5 hours and then allowed to stand for 20 hours. To establish the mercury level in the TEG, 2.15 g of the resulting liquid mixture was diluted using mercury free acetone, to dilution factor of 6. 1.5 ml of this solution was transferred to an autosampler vial and the mercury content measured using an HP6890 gas chromatograph connected to an atomic fluorescence detector. The level of elemental mercury in the TEG, after adjustment for the dilution, was found to be 2.90 ppm.

A quantity of a commercial granular mixed oxide absorbent, PURASPEC™ 2050, available from Johnson Matthey Catalysts, was sulphided by treating at room temperature with $H_2S$ (1%) flowing in methane at a 700 $hr^{-1}$ space velocity. The absorbent was taken to be fully sulphided when the $H_2S$ in the outlet gas and inlet gas streams were substantially the same and the colour of the sample had changed from green to black. The $H_2S$ was then removed from the inlet gas and the charge was then heated to 100° C. for about 2 hours in flowing methane to drive out any unreacted $H_2S$ from the absorbent structure. The sulphided absorbent was removed and stored in an airtight container.

0.5 ml of the sulphided absorbent was added to 5.0 ml of the mercury-containing TEG in a 20 ml vial, shaken vigorously, and left to stand overnight. A portion of the treated TEG was then removed from the mixture, diluted and analysed as described previously. The mercury content was found to be below the detection limit of 2.0 ppb w/v.

EXAMPLE 2

The method of Example 1 was followed using TEG to which water had been added to simulate the removal of mercury from "wet" TEG as would be found in a glycol dryer effluent. The results are shown below:

| Example | TEG (ml) | Water (%) | Absorbent (g) | Hg content (ppm) initial | Hg content (ppb) final |
|---------|----------|-----------|---------------|--------------------------|------------------------|
| 1 | 5.0 | — | 0.5 | 2.90 | <2.0 |
| 2 | 4.0 | 15.1 | 0.5 | 2.90 | <2.0 |

The invention claimed is:

1. A process for removing mercury compounds from a glycol- and/or alcohol-containing stream which contains said mercury compounds comprising the step of contacting said glycol- and/or alcohol-containing stream with a bed of solid absorbent particles, said absorbent particles comprising a sulphided metal or sulphur supported on a carbon support.

2. A process as claimed in claim 1, wherein said absorbent particles are said sulphided metal and said sulphided metal is selected from the group consisting of iron sulphide, copper sulphide and nickel sulphide or a mixture of said metal sulphides.

3. A process as claimed in claim 1, wherein said absorbent particles further comprise alumina or a refractory cement.

4. A process as claimed in claim 1, wherein said absorbent particles further comprise zinc oxide, zinc carbonate or zinc bicarbonate.

5. A process as claimed in claim 1 wherein said absorbent particles are said sulphided metal and said sulphided metal is formed by treating a metal compound with hydrogen sulphide, carbonyl sulphide, a mercaptan or a polysulphide.

6. A process as claimed in claim 1, wherein the glycol- and/or alcohol- containing stream is contacted with said solid absorbent particles at a pressure of less than or equal to 350 bar and a temperature which is less than or equal to 50° C.

7. A process as claimed in claim 1 wherein said absorbent particles are said sulphided metal and said sulphided metal is formed in situ in the absorbent bed by contacting an absorbent precursor with a sulphur-containing compound in the glycol- and/or alcohol-containing stream.

8. A process for removing water, sulphur compounds and/or carbon dioxide from a hydrocarbon-containing stream which additionally contains at least one compound of mercury or elemental mercury comprising:
   a) contacting the hydrocarbon stream with a liquid absorbent stream, comprising a glycol and/or an alcohol, thereby to absorb at least some of the water, sulphur compounds and/or carbon dioxide and mercury from the hydrocarbon stream into the liquid absorbent stream, to form a loaded liquid absorbent stream which contains mercury compounds; and
   b) removing said mercury compounds from said loaded liquid absorbent stream using a process as claimed in claim 1 to form a treated liquid absorbent stream containing a reduced concentration of mercury compared with the loaded liquid absorbent stream.

9. A process as claimed in claim 1, wherein said absorbent particles are said sulphided metal, and said sulphided metal is supported on a support material.

10. A process for removing water as claimed in claim 8 further comprising:
   c) drying the treated liquid absorbent stream.

11. A process for removing water as claimed in claim 10 further comprising recirculating the liquid absorbent stream from step c) to step a).

12. A process for removing water as claimed in claim 11, wherein the recirculating is done after mixing the liquid absorbent stream from step c) with a fresh liquid absorbent stream.

* * * * *